US011084857B2

(12) United States Patent
Jiang et al.

(10) Patent No.: US 11,084,857 B2
(45) Date of Patent: Aug. 10, 2021

(54) NSP-INTERLEUKIN-10 PROTEINS AND USES THEREOF

(71) Applicant: UNIVERSITY OF PITTSBURGH-OF THE COMMONWEALTH SYSTEM OF HIGHER EDUCATION, Pittsburgh, PA (US)

(72) Inventors: Yangzi Jiang, Pittsburgh, PA (US); Rocky S. Tuan, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 16/704,308

(22) Filed: Dec. 5, 2019

(65) Prior Publication Data

US 2020/0181219 A1 Jun. 11, 2020

Related U.S. Application Data

(60) Provisional application No. 62/775,433, filed on Dec. 5, 2018.

(51) Int. Cl.

| | |
|---|---|
| ***C07K 14/54*** | (2006.01) |
| ***C07K 14/48*** | (2006.01) |
| *A61K 38/00* | (2006.01) |

(52) U.S. Cl.

CPC .......... *C07K 14/5428* (2013.01); *C07K 14/48* (2013.01); *A61K 38/00* (2013.01); *C07K 2319/02* (2013.01)

(58) Field of Classification Search

CPC ................ C07K 14/5428; C07K 14/48; C07K 2319/02; A61K 38/00

See application file for complete search history.

(56) References Cited

U.S. PATENT DOCUMENTS 6,919,426 B2 7/2005 Boone et al.

FOREIGN PATENT DOCUMENTS

| | | |
|---|---|---|
| CA | 2529103 C | 11/2013 |
| EP | 2066336 | 9/2012 |
| WO | 2014023673 | 2/2014 |

OTHER PUBLICATIONS

Wang et al. "Novel anti-inflammatory target of geniposide: Inhibiting Itgβ1/Ras-Erk1/2 signal pathway via the miRNA-124a in rheumatoid arthritis synovial fibroblasts". International Immunopharmacology 65 (2018) 284-294. (Year: 2018).*

Joosten et al. "Role of Interleukin-4 and Interleukin-10 in Murine Collagen-Induced Arthritis". Arthritis and Rheumatism, vol. 40, No. 2, Feb. 1997, pp. 249-260. (Year: 1997).*

Seidel and Lane. "Control of Arthritis Pain with Anti-Nerve-Growth Factor: Risk and Benefit" Curr Rheumatol Rep (2012) 14:583-588. (Year: 2012).*

Tuveri et al. "NGF, a useful tool in the treatment of chronic vasculitic ulcers in rheumatoid arthritis". The Lancet, vol. 356, Nov. 18, 2000, p. 1739-1740. (Year: 2000).*

Altschul, Stephen F., et al. "Basic local alignment search tool." Journal of molecular biology 215.3 (1990): 403-410.

Altschul, Stephen F., et al. "Gapped BLAST and PSI-BLAST: a new generation of protein database search programs." Nucleic acids research 25.17 (1997): 3389-3402.

Henikoff, Steven, and Jorja G. Henikoff. "Amino acid substitution matrices from protein blocks." Proceedings of the National Academy of Sciences 89.22 (1992): 10915-10919.

Jiang, Y. & Tuan, R. S. Origin and function of cartilage stem/progenitor cells in osteoarthritis. Nat Rev Rheumatol, doi:10.1038/nrrheum.2014.200 (2014).

Jiang, Y. et al. Cartilage stem/progenitor cells are activated in osteoarthritis via interleukin-1beta/nerve growth factor signaling. Arthritis Res Ther 17, 327, doi:10.1186/s13075-015-0840-x (2015).

Karlin, Samuel, and Stephen F. Altschul. "Applications and statistics for multiple high-scoring segments in molecular sequences." Proceedings of the National Academy of Sciences 90.12 (1993): 5873-5877.

Lin, H., Cheng, A. W., Alexander, P. G., Beck, A. M. & Tuan, R. S. Cartilage tissue engineering application of injectable gelatin hydrogel with in situ visible-lightactivated gelation capability in both air and aqueous solution. Tissue Eng Part A 20, 2402-2411, doi:10.1089/ten.TEA.2013.0642 (2014).

Lin, H., Xue, J., Yin, W., Wang, B, Tuan, RS. BMP-2 gene and cell functionalized 3D scaffolds for the repair of cranial bone defect. Orthopaedic Research Society 2013 Annual Meeting, San Antonio, TX. (2013).

Lin, Hang, et al. "Projection stereolithographic fabrication of BMP-2 gene-activated matrix for bone tissue engineering." Scientific reports 7.1 (2017): 1-11.

Software for performing BLAST available at http://www.ncbi.nlm.nih.gov/ 2 pages.

Travaglia, A. et al. A small linear peptide encompassing the NGF N-terminus partly mimics the biological activities of the entire neurotrophin in PC12 cells. ACS chemical neuroscience 6, 1379-1392, doi:10.1021/acschemneuro.5b00069 (2015).

* cited by examiner

*Primary Examiner* — Adam Weidner
*Assistant Examiner* — Scott T. Humbarger
(74) *Attorney, Agent, or Firm* — Meunier Carlin & Curfman LLC

(57) ABSTRACT

Disclosed herein are Nsp-IL10 polypeptides comprising an Nsp polypeptide and an IL10 polypeptide. In some embodiments, Nsp-IL10 polypeptide is capable of activating an NGF signaling pathway, an IL10 signaling pathway, or both. Also disclosed are methods for treating a disease comprising administering an Nsp-IL10 polypeptide. The methods include treating diseases associated with joint inflammation, such as osteoarthritis.

13 Claims, 3 Drawing Sheets

Specification includes a Sequence Listing.

NSP-INTERLEUKIN-10 PROTEINS AND USES THEREOF

RELATED APPLICATIONS

This application claims priority to U.S. Application Ser. No. 62/775,433 filed Dec. 5, 2018. U.S. Application Ser. No. 62/775,433 is incorporated herein by reference in its entirety for all purposes.

FIELD

The disclosure generally relates to proteins, including fusion proteins, and methods for their use in treating diseases, particularly inflammatory diseases. Specifically, the disclosed polypeptides contain sequences from Nerve Growth Factor (NGF) and Interleukin-10.

BACKGROUND

Pain and loss of tissue function caused chronic inflammatory diseases has long been a major clinical challenge. For example, osteoarthritis (OA), the most prevalent degenerative joint disease worldwide, affects up to 20% of the population in the U.S., and is the most common cause of mobility loss, severely affecting the quality of life, work productivity, cost of healthcare. There is no cure for OA, and current clinical OA management is mainly concerned with symptom reduction, e.g., pain, swelling, stiffness, with oral non-steroidal anti-inflammatory drugs (NSAIDs) being the most commonly used pharmacological treatment at mid-stage of the disease, and arthroplasty, an irreversible procedure, as the final solution to maintain joint function. There are substantial gaps in the knowledge of the pathogenesis and effective interventions for early stage OA, which may prevent or delay disease development and maintain proper joint functions.

Interleukin-10 (IL10) exhibits a range of physiological properties, including anti-cancer and anti-tumor properties as well as having roles in inflammation. Dysregulation of IL10 is associated with autoimmune diseases and increased pathology in response to infection. Through a variety of mechanisms, IL10 produces anti-inflammatory responses which serve to modulate immune responses.

Nerve Growth Factor (NGF) was originally identified (and therefore named) based on its functions in promoting neuronal survival and differentiation. However, recent studies show that NGF functions in an array of biological processes. In particular, NGF has been implicated in the transmission and maintenance of persistent or chronic pain and inflammation. However, mechanisms by which NGF and NGF-derived polypeptides bind surface receptors may influence the signaling pathway and hence, overall response of activated cells.

While numerous factors are known to be involved in the control of inflammatory responses, the network of molecular interactions are poorly understood and thus, existing treatments are limited in their capacities to treat underlying causes of inflammation. The polypeptide compositions and methods disclosed herein address these and other needs.

SUMMARY

The present invention relates to polypeptides containing amino acid sequences derived from Nerve Growth Factor (NGF) and Interleukin-10 (IL-10; IL10) and methods for uses thereof. The present disclosure addresses at least a portion of the problems in the prior art by providing a polypeptide comprising an NGF polypeptide and an IL-10 polypeptide which can be co-expressed and used to treat various inflammatory conditions.

In one aspect, disclosed herein is an Nsp-IL10 polypeptide wherein Nsp is a portion of an NGF polypeptide that binds to an NGF receptor. In some embodiments, the Nsp polypeptide and the IL10 polypeptide are directly linked. In some embodiments, the polypeptide comprises a linker between the Nsp polypeptide and the IL10 polypeptide.

In another aspect, provided herein are methods of treating a subject with a disease comprising administering to the subject an Nsp-IL10 polypeptide comprising an Nsp polypeptide and an IL10 polypeptide. In some embodiments, the disease is an inflammatory disease, for instance, joint inflammation (e.g., osteoarthritis). In some embodiments, the method treats the disease by reducing inflammation, pain, tissue degeneration, or combinations thereof.

In another aspect, provided herein are kits comprising a vector comprising a polynucleotide sequence encoding an Nsp-IL10 polynucleotide operably linked to a gene promoter (referred to herein as promoter). The Nsp-IL10 polynucleotide comprises an Nsp polynucleotide and an IL10 polynucleotide.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are for purposes of example, are explanatory only, and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

FIG. 1A is a schematic showing organization of genetic elements in some Nsp-IL10 polypeptide expression constructs. FIG. 1B is a schematic showing predicted tertiary structure of an Nsp-IL10 polypeptide expressed from construct b in FIG. 1A. FIG. 1C is a schematic showing an Nsp-IL10 polypeptide binding cell-surface receptors in NGFR+ cells, found for example in a joint cavity.

FIG. 2A is a schematic showing an IL-10 expression plasmid usable for cloning Nsp-IL10 constructs. FIG. 2B is a schematic showing an Nsp-IL10 polypeptide construct and the results of a Western blot demonstrating expression of the construct in HEK293 cells.

DETAILED DESCRIPTION

Figures 1A, 1B, 1C:
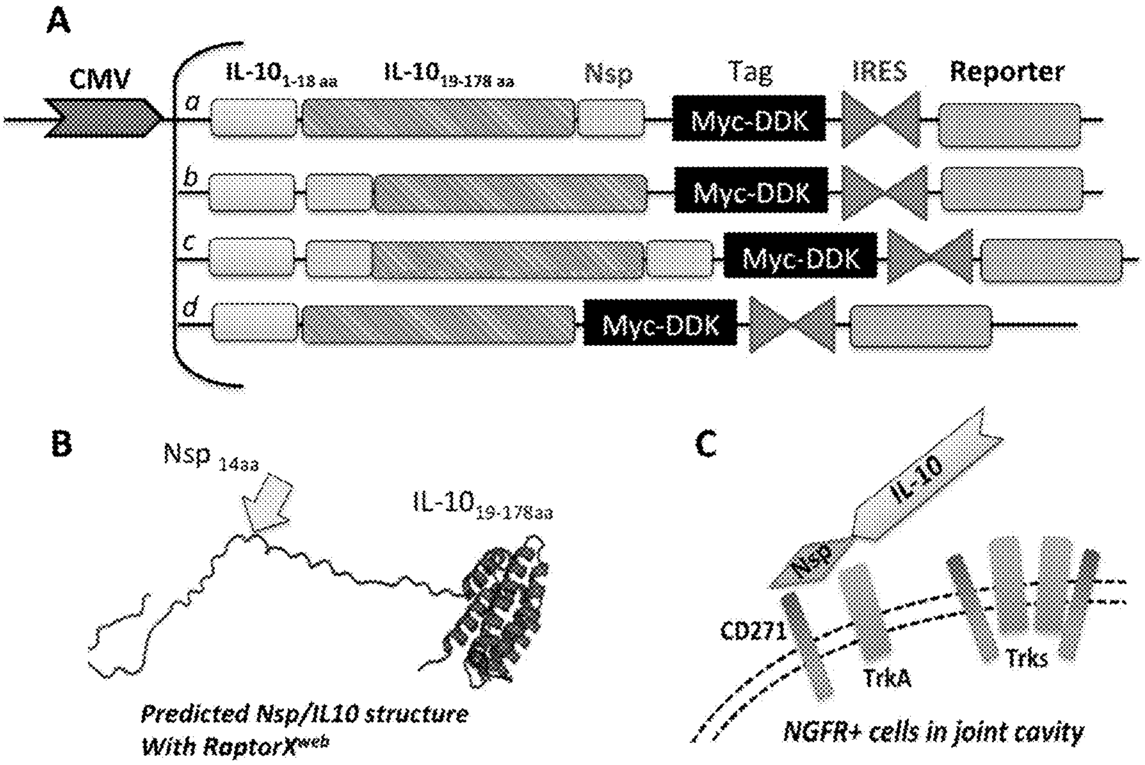
FIGS. 1A to 1C are schematics showing Nsp-IL10 polypeptide expression constructs and resultant Nsp-IL10 polypeptides.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular polypeptide is disclosed and discussed and a number of modifications that can be made to the polypeptide are discussed, specifically contemplated is each and every combination and permutation of the polypeptide and the modifications that are possible unless specifically indicated to the contrary. Thus, if a class of polypeptides A, B, and C are disclosed as well as a class of polypeptides D, E, and F and an example of a combination polypeptide, or, for example, a combination polypeptide comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Ranges can be expressed herein as from “about” one particular value, and/or to “about” another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as “about” that particular value in addition to the value itself. For example, if the value “10” is disclosed, then “about 10” is also disclosed.

As used in the specification and claims, the singular form “a,” “an,” and “the” include plural references unless the context clearly dictates otherwise. For example, the term “an agent” includes a plurality of agents, including mixtures thereof.

As used herein, the terms “may,” “optionally,” and “may optionally” are used interchangeably and are meant to include cases in which the condition occurs as well as cases in which the condition does not occur. Thus, for example, the statement that a formulation “may include an excipient” is meant to include cases in which the formulation includes an excipient as well as cases in which the formulation does not include an excipient.

“Administration” to a subject includes any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. “Concurrent administration”, “administration in combination”, “simultaneous administration” or “administered simultaneously” as used herein, means that the compounds are administered at the same point in time, overlapping in time, or essentially immediately following one another. In the latter case, the two compounds are administered at times sufficiently close that the results observed are indistinguishable from those achieved when the compounds are administered at the same point in time. “Systemic administration” refers to the introducing or delivering to a subject an agent via a route which introduces or delivers the agent to extensive areas of the subject’s body (e.g. greater than 50% of the body), for example through entrance into the circulatory or lymph systems. By contrast, “local administration” refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Due to redundancy in the genetic code, multiple codons can encode the same amino acid. Some organisms have a preference for using a particular codon to encode a particular amino acid, as determined by the percentage in which that particular amino acid is encoded by that particular codon throughout the organism's genome. Such optimization includes replacing at least one, or more than one, or a significant number, of codons with one or more codons that are more frequently used in the genes of that selected organism.

"Gene expression" and "protein expression" refer to the process by which polynucleotides are transcribed into mRNA and the process by which the transcribed mRNA is subsequently being translated into peptides, polypeptides, or proteins, respectively. If the polynucleotide is derived from genomic DNA, expression may include splicing of the mRNA in a eukaryotic cell.

"Identical" or percent "identity," in the context of two or more nucleic acids or polypeptide sequences, refer to two or more sequences or subsequences that are the same or have a specified percentage of amino acid residues or nucleotides that are the same (e.g., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The "linker" used herein refers to at least a bivalent moiety with a site of attachment for a first polypeptide and a site of attachment for a second polypeptide. For example, the first polypeptide or the second polypeptide can be attached to the linker at its N-terminus, its C-terminus or via a functional group on one of the side chains. The linker is sufficient to separate the first and the second polypeptides by at least one amino acid and in some embodiments by more than one amino acid. In some embodiments, the linker is sufficiently flexible to allow the first polypeptide to bind target molecules in a manner which is independent of the second polypeptide. In some embodiments, the linker is sufficiently flexible to allow the second polypeptide to bind target molecules in a manner which is independent of the first polypeptide. In some embodiments, the first polypeptide is an Nsp polypeptide and the second polypeptide is an IL-10 polypeptide. In some embodiments, the first polypeptide is an IL-10 polypeptide and the second polypeptide is an Nsp polypeptide.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In some embodiments, a promoter is operably linked with a coding sequence when it is capable of affecting (e.g. modulating relative to the absence of the promoter) the expression of a protein from that coding sequence (e.g., the coding sequence is under the transcriptional control of the promoter).

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule.

"Polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics.

"Specifically binds" when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

"Therapeutic agent" refers to any composition that has a beneficial biological effect. Beneficial biological effects include both therapeutic effects, e.g., treatment of a disorder or other undesirable physiological condition, and prophylactic effects, e.g., preventing symptoms of a disorder or other undesirable physiological condition (e.g., rheumatoid arthritis). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of chronic inflammation. Therapeutically effective amounts of a given therapeutic agent will typically vary with respect to factors such as the type and severity of the disorder or disease being treated and the age, gender, weight, and general condition of the subject. Thus, it is not always possible to specify a quantified "therapeutically effective amount." However, an appropriate "therapeutically effective amount" in any subject case may be determined by one of ordinary skill in the art using routine experimentation. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. It is understood that, unless specifically stated otherwise, a "therapeutically effective amount" of a therapeutic agent can also refer to an amount that is a prophylactically effective amount. In some instances, a desired biological or medical response is achieved following administration of multiple dosages of the composition to the subject over a period of days, weeks, or years.

As used herein, "transgene" refers to exogenous genetic material (e.g., one or more polynucleotides) that has been or can be artificially provided to a cell. The term can be used to refer to a "recombinant" polynucleotide encoding any of the herein disclosed polypeptides that are the subject of the present disclosure. The term "recombinant" refers to a sequence (e.g., polynucleotide or polypeptide sequence) which does not occur in the cell to be artificially provided with the sequence, or is linked to another polynucleotide in an arrangement which does not occur in the cell to be artificially provided with the sequence. It is understood that "artificial" refers to non-natural occurrence in the host cell and includes manipulation by man, machine, exogenous factors (e.g., enzymes, viruses, etc.), other non-natural manipulations, or combinations thereof. A transgene can comprise a gene operably linked to a promoter (e.g., an open reading frame), although is not limited thereto. Upon artificially providing a transgene to a cell, the transgene may integrate into the host cell chromosome, exist extrachromosomally, or exist in any combination thereof.

"Treat", "treating", "treatment" and grammatical variations thereof, in some instances include partially or completely reducing the severity of inflammation, reducing the overall area affected by inflammation, and reducing the duration of inflammation as compared with prior to treatment of the subject or as compared with the incidence of such symptom in a general or study population. "Treat", "treating", "treatment" and grammatical variations thereof, in some or further instances include partially or completely reducing the severity of arthritis (e.g., osteoarthritis), reducing the overall area affected by arthritis, and reducing the duration of arthritis as compared with prior to treatment of the subject or as compared with the incidence of such symptom in a general or study population.

"Vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. A plasmid is the most commonly used form of a vector; however, the invention is intended to include such other forms of vectors which serve equivalent function as and which are, or become, known in the art.

Nsp-IL10 Polypeptides

It should be understood that the Nsp-IL10 polypeptides of the present disclosure can be used in combination with the various compositions, methods, products, and applications disclosed herein.

In one aspect, disclosed herein are Nsp-IL10 polypeptides comprising an Nsp polypeptide and an IL10 polypeptide. A surprising discovery of the present invention is that these Nsp-IL10 polypeptides can coordinately or simultaneously activate both NGF and IL-10 signaling pathways. The Nsp-IL10 polypeptide, when administered to a subject, can treat chronic inflammatory diseases such as osteoarthritis. In some embodiments, the Nsp-IL10 polypeptide maintains tissue homeostasis and/or enhances immune modulation at least by reducing inflammation, pain, and/or delaying tissue degeneration. The herein disclosed Nsp-IL10 polypeptides are, in some embodiments, therefore capable of treating the underlying causes of chronic inflammatory diseases rather than simply reducing or ameliorating symptoms of such diseases.

As used herein, the term "Nsp" refers to an NGF small protein, or a portion of an NGF polypeptide that binds an NGF receptor (also called "NGFR"). "NGF" refers to a Nerve Growth Factor (NGF) polypeptide also known as NGFβ and, in humans, is encoded by the NGF gene. In some embodiments, the NGF polypeptide or polynucleotide is that identified in one or more publicly available databases as follows: HGNC: 7808, Entrez Gene: 4803, Ensembl: ENSG00000134259, OMIM: 162030, and UniProtKB: P01138. In some embodiments, the NGF polypeptide or polynucleotide comprises the sequence of SEQ ID NO: 1, or a polypeptide sequence having at or greater than about 80%, at or greater than about 85%, at or greater than about 90%, at or greater than about 95%, or at or greater than about 98% homology with SEQ ID NO: 1, or a fragment thereof. The NGF protein can be from any vertebrate, particularly from any mammal such as livestock such as cows, pigs, and sheep, primates such as humans, gorillas and monkeys, rodents such as mice, rats and guinea pigs, and other mammals such as horse, dog, bear, deer, dolphin, felines, etc. In some embodiments, the Nsp polypeptide is a portion of human NGF.

The Nsp polypeptide comprises a portion of an NGF polypeptide that binds an NGF receptor. The Nsp polypeptide can comprise more than one portion of NGF (e.g. an N-terminal portion and a C-terminal portion). In some embodiments, the Nsp polypeptide comprises the N-terminal half of NGF. Optionally, the Nsp polypeptide comprises the unstructured N-terminal domain of NGF. By "unstructured," it is meant the N-terminal domain lacks substantial alpha-helical or β-strand structure, and comprises primarily flexible loops with large degrees of freedom. In some embodiments, the Nsp polypeptide comprises amino acids 1-14 of NGF. In other embodiments, the Nsp polypeptide comprises amino acids 1-12, 1-13, 2-15, 3-16 or 4-17 of NGF.

In some embodiments, the Nsp polypeptide contains at least 60% (for example, at least 60%, at least 65%, at least 70%, at least 80%, at least 85%, at least 90%, at least 95%, at least 99%) identity to SEQ ID NO: 2. In some embodiments, the Nsp polypeptide comprises the amino acid sequence of SEQ ID NO: 2.

In some embodiments, a polynucleotide encoding the Nsp polypeptide comprises a nucleic acid sequence which is at least 60%, at least 75%, at least 80%, at least 85%, at least 90%, at least 95%, at least 98%, or at least 99% identical to SEQ ID NO: 9. In some embodiments, a polynucleotide encoding the Nsp polypeptide comprises SEQ ID NO: 9.

NGF is a polypeptide known to bind at least two receptors accessible at the outer surface of cell membranes: TrkA and p75NTR. In some embodiments, the NGF receptor is selected from a tyrosine kinase membrane receptor (Trk) and p75NTR. In some embodiments, the NGF receptor comprises Tyrosine kinase membrane Receptor A (TrkA). Accordingly, in some embodiments, the Nsp-IL10 polypeptide binds to TrkA or p75NTR. In some embodiments, the Nsp-IL10 polypeptide selectively binds TrkA (e.g., does not bind p75NTR). In some embodiments, the Nsp-IL10 polypeptide preferably binds TrkA as compared to p75NTR. In some embodiments, the Nsp-IL10 binding is agonistic. In other embodiments, the Nsp-IL10 binding is antagonistic. In some embodiments, the Nsp-IL10 polypeptide is capable of selectively binding TrkA without substantially activating the p75NTR-mediated apoptotic pathway. In some embodiments, binding of the Nsp-IL10 polypeptide to an NGF receptor activates an NGF signaling pathway. In some embodiments, binding of the Nsp-IL10 polypeptide to an NGF receptor facilitates (e.g., promotes) dimerization of the NGF receptor. In some embodiments, binding of the Nsp-IL10 polypeptide to an NGF receptor facilitates (e.g., promotes, increases) phosphorylation of the NGF receptor. In some embodiments, the phosphorylation comprises autophosphorylation. For example, in some embodiments, binding of NGF to TrkA results in dimerization and phosphorylation of TrkA, thereby initiating the NGF signaling pathway.

The NGF signaling pathway comprises several different signaling mediators, each having the potential to slightly or significantly alter the cellular response to binding of NGF or the Nsp polypeptide to an NGF receptor. For example, NGF-p75NTR binding can result in a signaling pathway which triggers apoptosis. Alternatively, NGF-TrkA binding can result in a signaling pathway which activates a mitogen activated protein kinase (MAPK; also known as extracellular signal-regulated kinase ERK) via ERK1/2 proteins. Alternatively, NGF-TrkA binding can result in a signaling pathway which activates a phosphoinositide 3-kinase. The phosphoinositide 3-kinase PI3K can phosphorylate and activate protein kinase B (PKB; also known as AKT). Activation of PI3K/AKT can result in cell protection, survival, and/or proliferation.

In some embodiments, the NGF signaling pathway comprises PI3K/AKT activation. In some or further embodiments, the NGF signaling pathway avoids p75NTR-mediated apoptosis, MAPK activation (ERK1/2 activation), or both. Thus, in some embodiments, the NGF signaling pathway includes only PI3K/AKT activation. In some embodiments, the Nsp-IL10 polypeptide selectively binds TrkA and selectively activates signaling via the PI3K/AKT pathway.

The Nsp-IL10 polypeptide disclosed herein further comprises an IL10 polypeptide. As used herein, "IL10" refers to Interleukin-10 or IL-10, an immune modulating cytokine. In some embodiments, the IL10 polypeptide or polynucleotide is that identified in one or more publicly available databases as follows: HGNC: 5962, Entrez Gene: 3586, Ensembl: ENSG00000136634, OMIM: 124092, and UniProtKB: P22301. In some embodiments, the IL10 polypeptide or polynucleotide comprises the sequence of SEQ ID NO: 3, or a polypeptide sequence having at or greater than about 80%, at or greater than about 85%, at or greater than about 90%, at or greater than about 95%, or at or greater than about 98% homology with SEQ ID NO: 3, or a fragment thereof.

As used herein, the term "IL10 polypeptide" refers to a polypeptide that comprises at least a portion of IL10, which portion binds an IL10 receptor. In some embodiments, the IL10 polypeptide comprises a full-length IL10 including a signal peptide. The polypeptide of SEQ ID NO: 5 is an exemplary signal peptide. In other embodiments, the IL10 polypeptide comprises a secreted form of IL10 (lacking a signal peptide). In some embodiments, the IL10 polypeptide is from any vertebrate, particularly from any mammal such as livestock such as cows, pigs, and sheep, primates such as humans, gorillas and monkeys, rodents such as mice, rats and guinea pigs, and other mammals such as horse, dog, bear, deer, dolphin, felines, etc.

In some embodiments, the IL10 polypeptide contains at least 60% (for example, at least 60%, at least 65%, at least 70%, at least 80%, at least 85%, at least 90%, at least 95%, at least 99%) identity to the amino acid sequence of SEQ ID NO: 4. In some embodiments, the IL10 polypeptide comprises the amino acid sequence of SEQ ID NO: 4.

In some embodiments, a polynucleotide encoding the IL10 polypeptide comprises a nucleic acid sequence which is at least 60%, at least 75%, at least 80%, at least 85%, at least 90%, at least 95%, at least 98%, or at least 99% identical to SEQ ID NO: 11. In some embodiments, a polynucleotide encoding the IL10 polypeptide comprises SEQ ID NO: 11.

In some embodiments, binding of the Nsp-IL10 peptide to an IL-10 receptor (IL-10R) activates an IL10 signaling pathway. The IL-10 receptor (IL-10R) can be tetrameric, being comprised of intracellular domains which bind JAK1 and TYK2 kinases. Subsequent autophosphorylation of these kinases activates Signal Transducer and Activator of Transcription (STAT) family proteins including STAT1 and STATS and primarily including STAT3. STAT activation leads to transcriptional regulation of an array of genes.

In some embodiments, Nsp-IL10 binding facilitates (e.g., promotes, increases) phosphorylation of IL-10R. In some embodiments, the phosphorylation comprises autophosphorylation. For example, binding of Nsp-IL10 to IL-10R results in phosphorylation of at least one of JAK1 and TYK2, thereby initiating the IL10 signaling pathway. Optionally, the IL10 signaling pathway comprises transcriptional inhibition of cytokine expression, for example, of pro-inflammatory cytokines. In some embodiments, the IL10 signaling pathway reduces expression of a cytokine selected from IFN-γ, IL-2, IL-3, TNFα and GM-CSF.

In some or further embodiments, the IL10 signaling pathway comprises increased expression of a deacetylase protein. Optionally, the deacetylase is NAD-dependent. In some or further embodiments, the IL10 signaling pathway comprises increased expression of a tissue aging marker. Optionally, the tissue aging marker is a sirtuin family protein (e.g., SIRT1, SIRT2, SIRT3, SIRT4, SIRT5, SIRT6, or SIRT7). Optionally, the tissue aging marker is Sirtuin1 (SIRT1).

Without wishing to be bound by any one particular mechanism, it is thought that the Nsp polypeptide in the Nsp-IL10 polypeptide functions to bind NGFR, thereby delivering the IL-10 polypeptide to NGFR+ cells. In some embodiments, binding of the Nsp polypeptide to NGFR activates an NGFR signaling pathway, while the IL-10 polypeptide activates an IL-10 signaling pathway in the same cell. In some embodiments, the Nsp-IL10 polypeptide activates the NGFR signaling pathway in one cell, and activates the IL-10 signaling pathway in a separate, adjacent or nearby cell.

The Nsp polypeptide and the IL10 polypeptide can be arranged within the Nsp-IL10 polypeptide in a number of ways. The Nsp polypeptide and the IL10 polypeptide can be expressed from separate genetic constructs. Alternatively, the Nsp polypeptide and the IL10 polypeptide can be expressed from the same genetic construct, for example as a single transcript.

In some embodiments, the Nsp polypeptide and the IL10 polypeptide are directly linked. By "directly linked," it is meant that the two polypeptides are covalently attached in a single macromolecule, where there are no intervening amino acids between the different polypeptides or where the individual polypeptides are connected to one another via one or more intervening amino acids (e.g., linkers). In some embodiments, the Nsp and IL10 polypeptides are directly linked in a single polypeptide, for example as a fusion protein comprising the Nsp and IL10 polypeptides. In some embodiments, the Nsp and IL10 polypeptides are directly linked by a post-translational modification, for example by a disulfide bridge (e.g., cysteine-cysteine disulfide bond).

In some embodiments, an Nsp polypeptide is directly linked to the N-terminal end of an IL10 polypeptide. In some embodiments, the Nsp polypeptide is directly linked to the C-terminal end of the IL10 polypeptide. In some embodiments, the continuous Nsp polypeptide is inserted within the sequence of an IL10 polypeptide, wherein the IL10 polypeptide includes an IL10 signal sequence. In some embodiments, the Nsp polypeptide is inserted within the sequence of the IL10 polypeptide C-terminal to the IL10 signal peptide but N-terminal to the IL10 mature, secreted polypeptide. In some embodiments, the Nsp polypeptide is inserted between the N-terminal $18^{th}$ and $19^{th}$ amino acids of an IL10 polypeptide which includes an IL10 signal sequence. In other embodiments, the Nsp polypeptide is directly linked to an IL10 polypeptide that does not comprise a signal peptide.

In some embodiments, the Nsp-IL10 polypeptide further comprises a linker. For example, the Nsp polypeptide may be linked to the IL10 polypeptide by an intervening linker comprising one or more amino acids. The linker can contain one, two, three, four, five, six, seven, eight, nine, ten, or a plurality of amino acids. The Nsp-IL10 polypeptide can comprise more than one linkers (e.g., one, two, three, four, five, six, seven, eight, nine, ten, or a plurality of linkers).

In some embodiments, a linker is between the Nsp polypeptide and the IL10 polypeptide. In some embodiments, the linker is positioned between an N-terminal Nsp polypeptide and a C-terminal IL10 polypeptide. Alternatively, the linker is positioned between a C-terminal Nsp polypeptide and an N-terminal IL10 polypeptide. In some embodiments, the continuous Nsp polypeptide is inserted within the sequence of the IL10 polypeptide, wherein a linker is positioned between the Nsp polypeptide and the IL10 polypeptide. In some embodiments, the Nsp polypeptide is inserted within the sequence of the IL10 polypeptide C-terminal to an IL10 signal peptide and N-terminal to an IL10 polypeptide, wherein a linker is positioned between the Nsp polypeptide and the IL10 polypeptide. In some embodiments, the Nsp polypeptide is inserted between the N-terminal $18^{th}$ and $19^{th}$ amino acids of the IL10 polypeptide, wherein a linker is positioned between the Nsp polypeptide and the IL10 polypeptide. In some embodiments, the polypeptide comprises an Nsp polypeptide flanked by two linkers inserted within the sequence of an IL10 polypeptide.

In some embodiments, the linker contains at least 60% (for example, at least 60%, at least 65%, at least 70%, at least 80%, at least 85%, at least 90%, at least 95%, at least 99%) identity to the amino acid sequence of SEQ ID NO: 6. In some embodiments, the linker comprises the amino acid sequence of SEQ ID NO: 6.

In some embodiments, a polynucleotide encoding the linker comprises a nucleic acid sequence which is at least 60%, at least 75%, at least 80%, at least 85%, at least 90%, at least 95%, at least 98%, or at least 99% identical to SEQ ID NO: 13. In some embodiments, a polynucleotide encoding the linker comprises SEQ ID NO: 13.

The Nsp-IL10 polypeptide can contain additional amino acid sequences which are not involved in activating either the NGF pathway or the IL10 pathway. For example, the Nsp-IL10 polypeptide can contain a signal peptide for export of the polypeptide from a biological cell. The signal peptide can be from a neurotrophin (e.g., NGF), IL10, or another exported protein. As another non-limiting example, the Nsp-IL10 polypeptide can contain additional sequences for affinity-based purification (e.g., Myc-DDK) and/or post-translational modifications (e.g., cysteines for forming disulfide bonds).

In some embodiments, the Nsp-IL10 polypeptide contains at least 60% (for example, at least 60%, at least 65%, at least 70%, at least 80%, at least 85%, at least 90%, at least 95%, at least 99%) identity to the amino acid sequence of SEQ ID NO: 7. In some embodiments, the Nsp-IL10 polypeptide comprises the amino acid sequence of SEQ ID NO: 7.

In some embodiments, a polynucleotide encoding the Nsp-IL10 polypeptide comprises a nucleic acid sequence which is at least 60%, at least 75%, at least 80%, at least 85%, at least 90%, at least 95%, at least 98%, or at least 99% identical to SEQ ID NO: 14. In some embodiments, a polynucleotide encoding the Nsp-IL10 polypeptide comprises SEQ ID NO: 14.

Functional IL10 is often in the form of a dimer. As such, the Nsp-IL10 polypeptide can comprise Nsp-IL10 polypeptide homodimers. Alternatively, the Nsp-IL10 polypeptide can comprise an IL10 polypeptide and Nsp-IL10 polypeptide heterodimer. As an example, FIG. 1B is a predicted structure of Nsp-IL10 polypeptide heterodimerized with IL10. In some embodiments, the Nsp-IL10 polypeptide can comprise a mixture of Nsp-IL10 polypeptide homodimers and heterodimers comprising IL10 polypeptide and Nsp-IL10 polypeptide.

The Nsp-IL10 polypeptide optionally comprises additional components such as amino acid sequences (e.g., sequences of other proteins, linker sequences, non-proteinogenic amino acids, etc.) and other protein-bound molecules (e.g., cofactors, small molecules, lipids, carbohydrates, nucleic acids, post-translational modifications such as acylation, glycosylation, hydroxylation, iodination, carbonylation, pegylation, etc.).

Also disclosed herein is a biological cell comprising an Nsp-IL10 polypeptide comprising an Nsp polypeptide and an IL10 polypeptide. For example, a host cell (e.g., *E. coli*, mammalian cells) can be used for production of the Nsp-IL10 polypeptide. Alternatively, the biological cell can be bound by an Nsp-IL10 polypeptide. For example, a biological cell in a cell culture, tissue culture, or in a subject can be bound by an Nsp-IL10 polypeptide via a cell-membrane receptor (e.g., NGFR, IL10R). The biological cell bound by an Nsp-IL10 polypeptide can be in various states of activation. For example, the biological cell may be bound but be non-activated for both NGF and IL10 pathways, bound and activated for either NGF or IL10 pathway but not both, or be activated for both NGF and IL10 pathways.

Also disclosed herein is a composition comprising an Nsp-IL10 polypeptide comprising an Nsp polypeptide and an IL10 polypeptide, and a pharmaceutically acceptable excipient. Suitable excipients include, but are not limited to, salts, diluents, binders, fillers, solubilizers, disintegrants, preservatives, sorbents, and other components. Also disclosed herein is a medicament comprising a pharmaceutically effective amount of an Nsp-IL10 polypeptide comprising an Nsp polypeptide and an IL10 polypeptide. As an example, a pharmaceutically effective amount of Nsp-IL10 polypeptide can be formulated in a hydrogel, particularly a photocrosslinkable and biodegradable hydrogel scaffold.

Methods of Treating

Also disclosed herein are methods of treating a subject with a disease comprising administering to the subject an Nsp-IL10 polypeptide comprising an Nsp polypeptide and an IL10 polypeptide or an Nsp-IL10 polynucleotide comprising an Nsp polynucleotide and an IL10 polynucleotide. The Nsp-IL10 polypeptide and polynucleotide can be any herein disclosed.

In some embodiments, the administering step can include any method of introducing the Nsp-IL10 polypeptide into the subject appropriate for the polypeptide formulation. The administering step can include at least one, two, three, four, five, six, seven, eight, nine, or at least ten dosages. The administering step can be performed before the subject exhibits disease symptoms (e.g., prophylactically), or during or after disease symptoms occur. The administering step can be performed prior to, concurrent with, or subsequent to administration of other agents to the subject. The administering step can be performed with or without co-administration of additional agents (e.g., immunosuppressive agents, additional anti-inflammation agents).

The administering step can comprise administering the Nsp-IL10 polypeptide as a purified polypeptide composition or in a cellular extract. In other embodiments, the administering step comprises administering a cell comprising a polynucleotide sequence encoding an Nsp-IL10 polynucleotide operably linked to a promoter, wherein the Nsp-IL10 polynucleotide comprises an Nsp polynucleotide and an IL10 polynucleotide, and expressing the polypeptide from the polynucleotide. In some embodiments, the cell is a chondrocyte. In some embodiments, the administering step comprises administering a polynucleotide sequence encoding an Nsp-IL10 polynucleotide operably linked to a promoter, wherein the Nsp-IL10 polynucleotide comprises an Nsp polynucleotide and an IL10 polynucleotide, and expressing the polypeptide from the polynucleotide. In some embodiments, the Nsp-IL10 polypeptide is expressed by a virus. Unless specifically stated otherwise, administering a polypeptide, as used herein, includes administering a polypeptide (e.g., in purified or extract form), administering a polynucleotide which encodes the polypeptide (e.g., a transgene), and administering both a polypeptide and a polynucleotide which encodes the polypeptide. Unless specifically stated otherwise, administering a polynucleotide, as used herein, includes administering a polynucleotide which encodes a polypeptide, and administering both a polypeptide and a polynucleotide which encodes the polypeptide.

The subject can be any mammalian subject, for example a human, dog, cow, horse, mouse, rabbit, etc. In some embodiments, the subject is a primate, particularly a human. The subject can be a male or female of any age, race, creed, ethnicity, socio-economic status, or other general classifiers.

The disease can be any disease in which administration of an Nsp-IL10 polypeptide can be used to treat. In some embodiments, the disease is an inflammatory disease. In some embodiments, the disease is chronic inflammation. Non-limiting examples of inflammatory diseases include joint inflammation (e.g., osteoarthritis), rheumatoid arthritis, collagen antibody-induced arthritis, asthma, chronic peptic ulcer, tuberculosis, periodontitis, ulcerative colitis, Crohn's disease, sinusitis, hepatitis, bronchitis, appendicitis, dermatitis, meningitis, ankylosing spondylitis, celiac disease, idiopathic pulmonary fibrosis, lupus, systemic lupus erythematosus, psoriasis, type 1 diabetes, Addison's disease, allergy, arthritis, prostatitis, diverticulitis, glomerulonephritis, hidradenitis suppurativa, inflammatory bowel disease, interstitial cystitis, mast cell activation syndrome, mastocytosis, otitis, pelvic inflammatory disease, reperfusion injury, rheumatic fever, rhinitis, sarcoidosis, transplant rejection, vasculitis, atherosclerosis, gout, pleurisy, eczema, gastritis, splenitis, laryngitis, thyroiditis, pharyngitis, multiple sclerosis, myopathies, seborrheic dermatitis, Wegener's granulomatosis, acne vulgaris, Alzheimer's disease, autoimmune diseases, hypersensitivities, Parkinson's disease, etc., and combinations thereof.

The method can include systemic administration of the Nsp-IL10 polypeptide or polynucleotide. Alternatively, the method can include local administration of the Nsp-IL10 polypeptide or polynucleotide. For example, the Nsp-IL10 polypeptide or polynucleotide can be administered locally to areas of inflammation such as inflamed joints. In some embodiments, the Nsp-IL10 polypeptide or polynucleotide is administered to areas of the subject comprising chondrocytes.

In some embodiments, the method treats the disease by reducing inflammation, pain, tissue degeneration, or combinations thereof. In some embodiments, the method reduces inflammation locally in areas affected by osteoarthritis. In some embodiments, the method treats the disease by activating an NGF signaling pathway, an IL10 signaling pathway, or combinations thereof. In some embodiments, the method increases phosphorylation of TrkA, increases expression of SIRT1, increases phosphorylation of cAMP response element-binding protein (CREB), or combinations thereof.

In some embodiments, the method includes treating a subject with a disease comprising administering to the subject a medicament comprising an Nsp-IL10 polypeptide comprising an Nsp polypeptide and an IL10 polypeptide. Generally, the medicament comprises a pharmaceutically acceptable excipient and a pharmaceutically effective amount of an Nsp-IL10 polypeptide comprising an Nsp polypeptide and an IL10 polypeptide.

Also disclosed herein are methods of activating an anti-inflammatory signaling pathway in a biological cell comprising administering to the cell an Nsp-IL10 polypeptide comprising an Nsp polypeptide and an IL10 polypeptide. The anti-inflammatory signaling pathway can comprise an NGF pathway or an IL10 pathway. In some embodiments, both an NGF pathway and an IL10 pathway are activated. In some embodiments, the biological cell is a human cell. In some embodiments, the cell is a chondrocyte.

Kits

Also disclosed herein are kits comprising a vector comprising a polynucleotide sequence encoding an Nsp-IL10 polynucleotide operably linked to a promoter. The Nsp-10 polynucleotide comprises an Nsp polynucleotide and an IL10 polynucleotide.

In some embodiments, the NGF polypeptide or polynucleotide is that identified in one or more publicly available databases as follows: HGNC: 7808, Entrez Gene: 4803, Ensembl: ENSG00000134259, OMIM: 162030, and UniProtKB: P01138. In some embodiments, the NGF polynucleotide comprises the sequence of SEQ ID NO: 8, or a polynucleotide sequence having at or greater than about 80%, at or greater than about 85%, at or greater than about 90%, at or greater than about 95%, or at or greater than about 98% homology with SEQ ID NO: 8. The NGF polynucleotide can be from any vertebrate, particularly from any mammal such as livestock such as cows, pigs, and sheep, primates such as humans, gorillas and monkeys, rodents such as mice, rats and guinea pigs, and other mammals such as horse, dog, bear, deer, dolphin, felines, etc. In some embodiments, the Nsp polynucleotide is a portion of human NGF.

The Nsp polynucleotide can encode more than one portion of NGF (e.g. an N-terminal portion and a C-terminal portion). In some embodiments, the Nsp polynucleotide encodes the N-terminal half of NGF. Optionally, the Nsp polynucleotide encodes the unstructured N-terminal domain of NGF. In some embodiments, the Nsp polynucleotide encodes amino acids 1-14 of NGF.

In some embodiments, the Nsp polynucleotide contains at least 60% (for example, at least 60%, at least 65%, at least 70%, at least 80%, at least 85%, at least 90%, at least 95%, at least 99%) identity to SEQ ID NO: 9. In some embodiments, the Nsp polynucleotide comprises the sequence of SEQ ID NO: 9.

In some embodiments, the IL10 polynucleotide encodes a full-length IL10 including a signal peptide. In other embodiments, the IL10 polynucleotide encodes a form of IL10 lacking a signal peptide. In some embodiments, the IL10 polynucleotide is from any vertebrate, particularly from any mammal such as livestock such as cows, pigs, and sheep, primates such as humans, gorillas and monkeys, rodents such as mice, rats and guinea pigs, and other mammals such as horse, dog, bear, deer, dolphin, felines, etc.

In some embodiments, a polynucleotide encoding the IL10 polypeptide comprises a nucleic acid sequence which is at least 60%, at least 75%, at least 80%, at least 85%, at least 90%, at least 95%, at least 98%, or at least 99% identical to SEQ ID NO: 11. In some embodiments, a polynucleotide encoding the IL10 polypeptide comprises SEQ ID NO: 11.

In some embodiments, the Nsp-IL10 polynucleotide further comprises a linker. For example, the Nsp polynucleotide may be linked to the IL10 polynucleotide by an intervening linker comprising one or more nucleotides. The linker can contain one, two, three, four, five, six, seven, eight, nine, ten, or a plurality of nucleotides. The Nsp-IL10 polynucleotide can comprise more than one linkers (e.g., one, two, three, four, five, six, seven, eight, nine, ten, or a plurality of linkers).

In some embodiments, a linker is between the Nsp polynucleotide and the IL10 polynucleotide. In some embodiments, the linker is positioned between a 5' end of an Nsp polynucleotide and a 3' end of a IL10 polynucleotide. Alternatively, the linker is positioned between a 3' end of an Nsp polynucleotide and a 5' end of a IL10 polynucleotide. In some embodiments, the continuous Nsp polynucleotide is inserted within the sequence of the IL10 polynucleotide, wherein a linker is positioned between the Nsp polynucleotide and the IL10 polynucleotide. In some embodiments, the Nsp polynucleotide is inserted within the sequence of the IL10 polynucleotide 3' to an IL10 signal peptide and 5' to an IL10 polynucleotide, wherein a linker is positioned between the Nsp polynucleotide and the IL10 polynucleotide. In some embodiments, the polynucleotide comprises an Nsp polynucleotide flanked by two linkers inserted within the sequence of an IL10 polynucleotide.

In some embodiments, a polynucleotide encoding the linker comprises a nucleic acid sequence which is at least 60%, at least 75%, at least 80%, at least 85%, at least 90%, at least 95%, at least 98%, or at least 99% identical to SEQ ID NO: 13. In some embodiments, a polynucleotide encoding the linker comprises SEQ ID NO: 13.

In some embodiments, a polynucleotide encoding the Nsp-IL10 polypeptide comprises a nucleic acid sequence which is at least 60%, at least 75%, at least 80%, at least 85%, at least 90%, at least 95%, at least 98%, or at least 99% identical to SEQ ID NO: 14. In some embodiments, a polynucleotide encoding the Nsp-IL10 polypeptide comprises SEQ ID NO: 14.

Non-limiting examples of vectors that can be used to introduce expression vectors that encode Nsp-10 polypeptide in various cell types: a nucleic acid vector (e.g., a plasmid vector) encoding Nsp-10 polypeptide can be delivered directly to bacterial cells or cultured cells (e.g., mammalian cells) by electroporation; a polynucleotide vector (e.g., a plasmid vector) encoding Nsp-10 polypeptide can be delivered directly to bacterial cells by chemical transformation; a viral vector (e.g., a retroviral vector, adenoviral vector, an adeno associated viral vector, an alphavirus vector, a vaccinia viral vector, a herpes viral vector, etc., as are known in the art) comprising a polynucleotide sequence encoding Nsp-10 polypeptide can be used to deliver Nsp-10 polypeptide to cells (e.g., mammalian cells); a baculovirus expression system can be used to deliver Nsp-10 polypeptide to insect cells; *Agrobacterium* mediated delivery can be employed in plants; and/or lipid mediated delivery (e.g., lipofectamine, oligofectamine) can also be employed for mammalian cells.

In some embodiments, the gene sequence (for example, of a gene expressing Nsp-10 polypeptide) may be codon optimized, without changing the resulting polypeptide sequence. In some embodiments, the codon optimization includes replacing at least one, or more than one, or a significant number, of codons with one or more codons that are more frequently used in various organisms. In some embodiments, the codon optimization increases expression of the optimized gene sequence.

EXAMPLES

To further illustrate the principles of the present disclosure, the following examples are put forth so as to provide those of ordinary skill in the art with a complete disclosure and description of how the compositions, articles, and methods claimed herein are made and evaluated. They are not intended to limit the scope of the present invention. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1. Development and Functional Analysis of Nsp-IL10 Polypeptide Expression System in Chondrocytes The polypeptide Nsp-IL10 can be constructed in numerous ways. Several embodiments of an Nsp-IL10 polypeptide containing the NGFR targeted domain NGF Small Peptide ("Nsp") inserted at the N- and/or C-terminus of an IL10 polypeptide are shown in FIG. 1A. The expression constructs can contain, for example, a Myc-DDK tag for purification and/or identification purposes. A cytomegalovirus (CMV) promoter is an example promoter which can be used to drive expression of the polypeptide mRNA. Three example construct strategies (a, b, and c) are shown, representing different placements of an Nsp sequence within the recombinant construct. Strategy a includes fusion of an Nsp sequence at the C-terminal end of an IL10 polypeptide. Strategy b, further detailed in FIG. 2, includes insertion of an Nsp sequence at the N-terminus of an IL10 polypeptide and at the C-terminal end of an IL10 signal peptide. Strategy c includes a combination of strategies a and b. Item d depicts the human IL-10 vector control, in which no Nsp sequence is included. Internal ribosome entry sites (IRES) are included in each construct, which can drive expression of a reporter gene to track transcription of the overall construct. Any reporter gene capable of tracking transcription can be used; for example, green fluorescent protein (Gfp).

The predicted protein structure of Nsp-IL10 construct b from RaptorX shows no conformational change in IL-10 in polypeptide expression strategy b (FIG. 1B). Amino acids 19-178 of IL-10 retain native structure, despite insertion of the Nsp sequence near the N-terminus of IL-10.

Because Nsp specifically binds NGFR, Nsp functions to target Nsp-IL10 polypeptide to NGFR for specific delivery of IL-10 to NGFR+ cells (FIG. 1C). Nsp specifically binds the NGF receptor TrkA, thereby additionally positioning IL-10 adjacent to NGFR+ cells. Thus, Nsp-IL10 polypeptide is capable of activating both the NGFR and IL-10 signaling pathways, either in the same cell or in separate, adjacent or nearby cells.

Figures 2A, 2B:
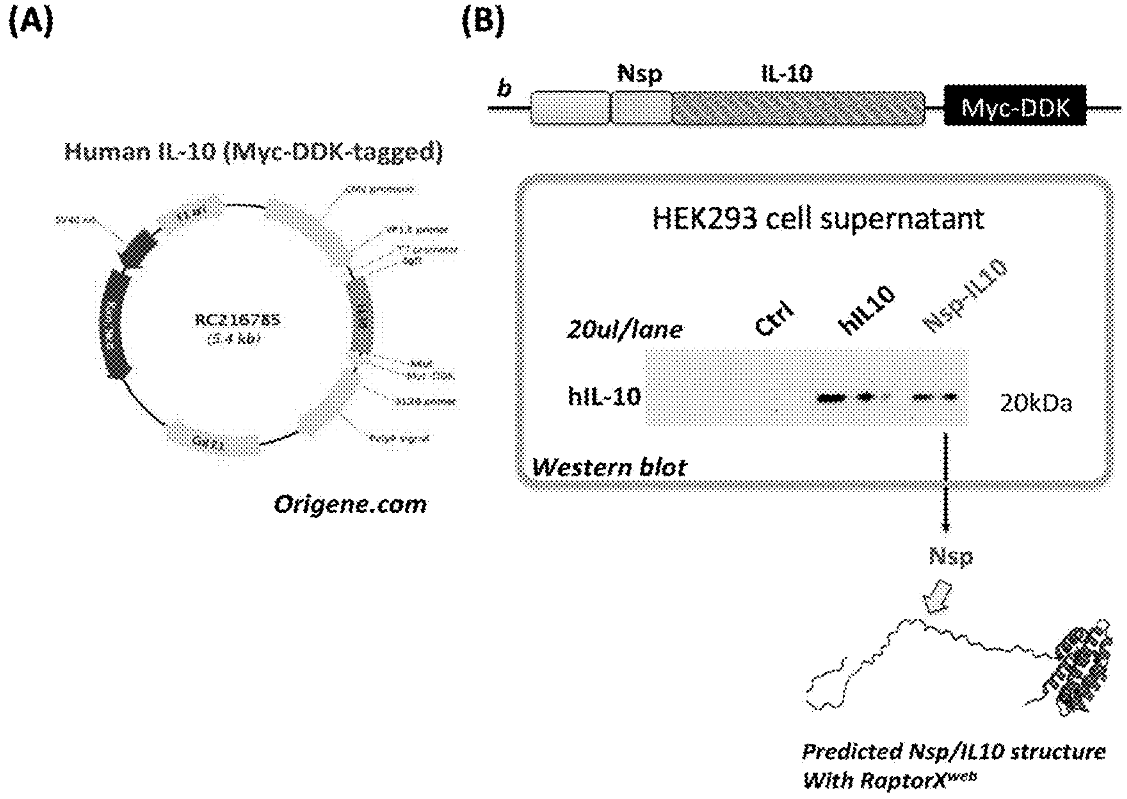
FIGS. 2A and 2B depict a strategy for expression of an Nsp-IL10 polypeptide.
Figure 3:
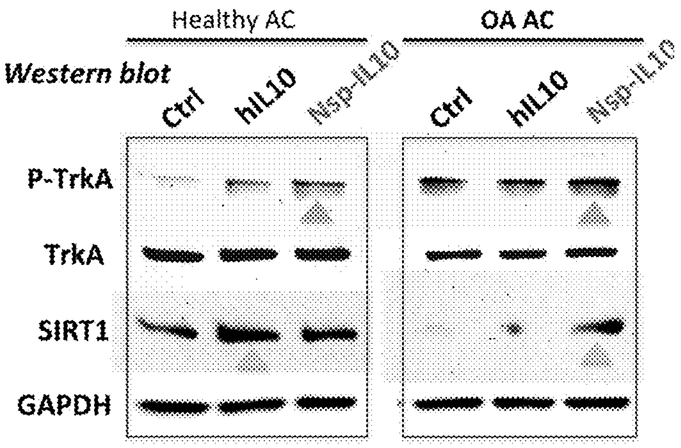
FIG. 3 is an immunoblot showing the downstream effects (expression of P-TrkA, TrkA, SIRT1 and GAPDH) of Nsp-IL10 polypeptide expression in healthy (left) and diseased (osteoarthritis; right) articular chondrocytes (AC) via Western blot analysis.

Plasmid-based transgene constructs can be sub-cloned into viral vectors, which can be transduced into mammalian cells for efficient, heterologous expression of proteins. An example construct used for Nsp-IL10 polypeptide construction and expression in mammalian cells is shown in FIG. 2A. In one example embodiment, strategy b of FIG. 1A was used to develop an Nsp-IL10 polypeptide and determine expression in human cells (FIG. 2B). The Nsp sequence was placed at the N-terminus of IL10 polypeptide lacking a signal peptide and at the C-terminus of an IL10 signal peptide in a human IL-10 expression construct. The construct further contained a Myc-DDK tag for purification and/or identification purposes. The gene construct was transduced into a HEK293 cell line and analyzed for expression (FIG. 2B). IL-10 Western blot analysis of supernatants from cultures of HEK293 cells showed results from cells harboring non-transgene control (Ctrl), human IL-10 transgene (hIL10) and Nsp-IL10 polypeptide transgene (Nsp-IL10), respectively.

The function of Nsp-IL10 protein from HEK293 culture medium was analyzed. Primary isolated human derived articular chondrocytes (AC) were used as reporter cells of NGF and IL-10 signaling. ACs were isolated from healthy ("Healthy AC") and diseased ("OA AC") areas of the same total knee joint replacement patient. ACs were treated with Nsp-IL10-containing medium for 48 hours. Western blot analysis showed that within 48 hours Nsp-IL10 treatment activated the NGF receptor Tyrosine kinase membrane receptor A (TrkA), as shown by appearance of phosphorylated TrkA (p-TrkA). Further, expression of a marker gene related to the control of cellular aging, Sirtuin 1 (SIRT1) was enhanced with IL-10 treatment compared to untreated controls (Ctrl). SIRT1 inhibits apoptosis and enhances survival of human OA chondrocytes. Results of p-TrkA and SIRT1 Western blot analysis indicated simultaneous activation of both NGF and IL10 mediated signaling pathways. P2, DMEM:F12 1:1, 10% fetal bovine serum (FBS) was used as the HEK293 cell culture conditions. Cultures were grown to full confluence, then pre-incubated in 2% FBS hDMEM for 24 hours. Cells were then removed by centrifugation, and culture medium was added to AC cultures for 48 hours. Anti-GAPDH antibody was used as a loading control in Western blot experiments.

REFERENCES

Jiang, Y. & Tuan, R. S. Origin and function of cartilage stem/progenitor cells in osteoarthritis. Nat Rev Rheumatol, doi:10.1038/nrrheum.2014.200 (2014).

Jiang, Y. et al. Cartilage stem/progenitor cells are activated in osteoarthritis via interleukin-1 beta/nerve growth factor signaling. Arthritis Res Ther 17, 327, doi:10.1186/s13075-015-0840-x (2015).

Travaglia, A. et al. A small linear peptide encompassing the NGF N-terminus partly mimics the biological activities of the entire neurotrophin in PC12 cells. ACS chemical neuroscience 6, 1379-1392, doi:10.1021/acschemneuro.5b00069 (2015).

Lin, H., Cheng, A. W., Alexander, P. G., Beck, A. M. & Tuan, R. S. Cartilage tissue engineering application of injectable gelatin hydrogel with in situ visible-light-activated gelation capability in both air and aqueous solution. Tissue Eng Part A 20, 2402-2411, doi:10.1089/ten.TEA.2013.0642 (2014).

Lin, H., Xue, J., Yin, W., Wang, B, Tuan, R S. BMP-2 gene and cell-functionalized 3D scaffolds for the repair of cranial bone defect. Orthopaedic Research Society 2013 Annual Meeting, San Antonio, Tex. (2013).

Example 2. Sequences

An NGF amino acid sequence

SEQ ID NO: 1

```
MSMLFYTLITAFLIGIQAEPHSESNVPAGHTIPQAHWTKLQHSLDTALRRARSAPAAAIA

ARVAGQTRNITVDPRLFKKRRLRSPRVLFSTQPPREAADTQDLDFEVGGAAPFNRTHRS

KRSSSHPIFHRGEFSVCDSVSVWVGDKTTATDIKGKEVMVLGEVNINNSVFKQYFFETK

CRDPNPVDSGCRGIDSKHWNSYCTTTHTFVKALTMDGKQAAWRFIRIDTACVCVLSRK

AVRRA
```

-continued

An Nsp amino acid sequence

SEQ ID NO: 2

SSSHPIFHRGEFSV

An IL-10 amino acid sequence.

SEQ ID NO: 3

MHSSALLCCLVLLTGVRASPGQGTQSENSCTHFPGNLPNMLRDLRDAFSRVKTFFQMK

DQLDNLLLKESLLEDFKGYLGCQALSEMIQFYLEEVMPQAENQDPDIKAHVNSLGENLK

TLRLRLRRCHRFLPCENKSKAVEQVKNAFNKLQEKGIYKAMSEFDIFINYIEAYMTMKIR

N

An IL-10 amino acid sequence

SEQ ID NO: 4

SPGQGTQSENSCTHFPGNLPNMLRDLRDAFSRVKTFFQMKDQLDNLLLKESLLEDFKGY

LGCQALSEMIQFYLEEVMPQAENQDPDIKAHVNSLGENLKTLRLRLRRCHRFLPCENKS

KAVEQVKNAFNKLQEKGIYKAMSEFDIFINYIEAYMTMKIRN

An IL-10 amino acid sequence

SEQ ID NO: 5

MHSSALLCCLVLLTGVRA

A linker amino acid sequence

SEQ ID NO: 6

GGSG

An Nsp-IL10 polypeptide amino acid sequence

SEQ ID NO: 7

MHSSALLCCLVLLTGVRAGGSGSSSHPIFHRGEFSVGGSGSPGQGTQSENSCTHFPGNLP

NMLRDLRDAFSRVKTFFQMKDQLDNLLLKESLLEDFKGYLGCQALSEMIQFYLEEVMP

QAENQDPDIKAHVNSLGENLKTLRLRLRRCHRFLPCENKSKAVEQVKNAFNKLQEKGIY

KAMSEFDIFINYIEAYMTMKIRN

A DNA sequence encoding the NGF polypeptide of
SEQ ID NO: 1

SEQ ID NO: 8

ATGTCCATGTTGTTCTACACTCTGATCACAGCTTTTCTGATCGGCATACAGGCGGAA

CCACACTCAGAGAGCAATGTCCCTGCAGGACACACCATCCCCCAAGCCCACTGGAC

TAAACTTCAGCATTCCCTTGACACTGCCCTTCGCAGAGCCCGCAGCGCCCCGGCAGC

GGCGATAGCTGCACGCGTGGCGGGGCAGACCCGCAACATTACTGTGGACCCCAGGC

TGTTTAAAAAGCGGCGACTCCGTTCACCCCGTGTGCTGTTTAGCACCCAGCCTCCCC

GTGAAGCTGCAGACACTCAGGATCTGGACTTCGAGGTCGGTGGTGCTGCCCCCTTCA

ACAGGACTCACAGGAGCAAGCGGTCATCATCCCATCCCATCTTCCACAGGGGCGAA

TTCTCGGTGTGTGACAGTGTCAGCGTGTGGGTTGGGGATAAGACCACCGCCACAGAC

ATCAAGGGCAAGGAGGTGATGGTGTTGGGAGAGGTGAACATTAACAACAGTGTATT

CAAACAGTACTTTTTTGAGACCAAGTGCCGGGACCCAAATCCCGTTGACAGCGGGTG

CCGGGGCATTGACTCAAAGCACTGGAACTCATATTGTACCACGACTCACACCTTTGT

CAAGGCGCTGACCATGGATGGCAAGCAGGCTGCCTGGCGGTTTATCCGGATAGATA

CGGCCTGTGTGTGTGTGCTCAGCAGGAAGGCTGTGAGAAGAGCCTGA

A DNA sequence encoding the Nsp polypeptide of
SEQ ID NO: 2

SEQ ID NO: 9

TCATCATCCCATCCCATCTTCCACAGGGGCGAATTCTCGGTG

A DNA sequence encoding the IL-10 polypeptide of
SEQ ID NO: 3

SEQ ID NO: 10

ATGCACAGCTCAGCACTGCTCTGTTGCCTGGTCCTCCTGACTGGGGTGAGGGCCAGC

CCAGGCCAGGGCACCCAGTCTGAGAACAGCTGCACCCACTTCCCAGGCAACCTGCC

-continued

TAACATGCTTCGAGATCTCCGAGATGCCTTCAGCAGAGTGAAGACTTTCTTTCAAAT

GAAGGATCAGCTGGACAACTTGTTGTTAAAGGAGTCCTTGCTGGAGGACTTTAAGG

GTTACCTGGGTTGCCAAGCCTTGTCTGAGATGATCCAGTTTTACCTGGAGGAGGTGA

TGCCCCAAGCTGAGAACCAAGACCCAGACATCAAGGCGCATGTGAACTCCCTGGGG

GAGAACCTGAAGACCCTCAGGCTGAGGCTACGGCGCTGTCATCGATTTCTTCCCTGT

GAAAACAAGAGCAAGGCCGTGGAGCAGGTGAAGAATGCCTTTAATAAGCTCCAAGA

GAAAGGCATCTACAAAGCCATGAGTGAGTTTGACATCTTCATCAACTACATAGAAG

CCTACATGACAATGAAGATACGAAACTGA

A DNA sequence encoding the IL10 amino acid sequence of SEQ ID NO: 4

SEQ ID NO: 11

AGCCCAGGCCAGGGCACCCAGTCTGAGAACAGCTGCACCCACTTCCCAGGCAACCT

GCCTAACATGCTTCGAGATCTCCGAGATGCCTTCAGCAGAGTGAAGACTTTCTTTCA

AATGAAGGATCAGCTGGACAACTTGTTGTTAAAGGAGTCCTTGCTGGAGGACTTTAA

GGGTTACCTGGGTTGCCAAGCCTTGTCTGAGATGATCCAGTTTTACCTGGAGGAGGT

GATGCCCCAAGCTGAGAACCAAGACCCAGACATCAAGGCGCATGTGAACTCCCTGG

GGGAGAACCTGAAGACCCTCAGGCTGAGGCTACGGCGCTGTCATCGATTTCTTCCCT

GTGAAAACAAGAGCAAGGCCGTGGAGCAGGTGAAGAATGCCTTTAATAAGCTCCAA

GAGAAAGGCATCTACAAAGCCATGAGTGAGTTTGACATCTTCATCAACTACATAGA

AGCCTACATGACAATGAAGATACGAAACTGA

A DNA sequence encoding the IL10 amino acid sequence of SEQ ID NO: 5

SEQ ID NO: 12

ATGCACAGCTCAGCACTGCTCTGTTGCCTGGTCCTCCTGACTGGGGTGAGGGCC

A DNA sequence encoding the linker amino acid sequence of SEQ ID NO: 6

SEQ ID NO: 13

GGAGGATCAGGC

A DNA sequence encoding the Nsp-IL10 polypeptide of SEQ ID NO: 7

SEQ ID NO: 14

ATGCACAGCTCAGCACTGCTCTGTTGCCTGGTCCTCCTGACTGGGGTGAGGGCCGGA

GGATCAGGCTCATCATCCCATCCCATCTTCCACAGGGGCGAATTCTCGGTGGGAGGA

TCAGGCAGCCCAGGCCAGGGCACCCAGTCTGAGAACAGCTGCACCCACTTCCCAGG

CAACCTGCCTAACATGCTTCGAGATCTCCGAGATGCCTTCAGCAGAGTGAAGACTTT

CTTTCAAATGAAGGATCAGCTGGACAACTTGTTGTTAAAGGAGTCCTTGCTGGAGGA

CTTTAAGGGTTACCTGGGTTGCCAAGCCTTGTCTGAGATGATCCAGTTTTACCTGGA

GGAGGTGATGCCCCAAGCTGAGAACCAAGACCCAGACATCAAGGCGCATGTGAACT

CCCTGGGGGAGAACCTGAAGACCCTCAGGCTGAGGCTACGGCGCTGTCATCGATTT

CTTCCCTGTGAAAACAAGAGCAAGGCCGTGGAGCAGGTGAAGAATGCCTTTAATAA

GCTCCAAGAGAAAGGCATCTACAAAGCCATGAGTGAGTTTGACATCTTCATCAACTA

CATAGAAGCCTACATGACAATGAAGATACGAAACTGA

Publications cited herein are hereby specifically incorporated by reference in their entireties and at least for the material for which they are cited.

It should be understood that, while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

We claim:

1. A method of treating joint inflammation in a subject comprising administering to the subject a therapeutically effective amount of an Nsp-IL10 polypeptide comprising an Nsp polypeptide and an IL10 polypeptide, wherein the Nsp polypeptide is at least 90% identical to the full length of SEQ ID NO: 2, and wherein the administration results in a reduction of the joint inflammation in the subject.

2. The method of claim 1, wherein the Nsp polypeptide consists of SEQ ID NO: 2.

3. The method of claim 1, wherein the IL10 polypeptide comprises SEQ ID NO: 4.

4. The method of claim 1, wherein the joint inflammation is chronic.

5. The method of claim 1, wherein the joint inflammation comprises osteoarthritis.

6. The method of claim 1, wherein the administration of the Nsp-IL10 polynucleotide results in activation of an NGF signaling pathway and an IL-10 signaling pathway.

7. The method of claim 1, wherein the method increases phosphorylation of TrkA, increases expression of SIRT1, increases phosphorylation of CREB, or combinations thereof.

8. The method of claim 1, wherein the Nsp-IL10 polypeptide further comprises a signal peptide having a sequence of SEQ ID NO: 5.

9. The method of claim 1, wherein the Nsp-IL10 polypeptide further comprises one or more linkers.

10. The method of claim 9, wherein the one or more linkers is between the Nsp polypeptide and the IL10 polypeptide.

11. The method of claim 9, wherein the one or more linkers comprises SEQ ID NO: 6.

12. The method of claim 1, wherein the Nsp-IL10 polypeptide comprises SEQ ID NO: 7.

13. The method of claim 1, wherein the method further treats tissue degeneration and the administration further results in a reduction of tissue degeneration in the subject.

* * * * *

SEQUENCE LISTING

<160> NUMBER OF SEQ ID NOS: 14

<210> SEQ ID NO 1
<211> LENGTH: 241
<212> TYPE: PRT
<213> ORGANISM: Homo sapiens

<400> SEQUENCE: 1

```
Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Ala His Trp Thr Lys Leu Gln His Ser Leu Asp Thr Ala Leu
        35                  40                  45

Arg Arg Ala Arg Ser Ala Pro Ala Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

Ala
```

<210> SEQ ID NO 2
<211> LENGTH: 14
<212> TYPE: PRT
<213> ORGANISM: Artificial Sequence
<220> FEATURE:
<223> OTHER INFORMATION: Synthetic construct

<400> SEQUENCE: 2

```
Ser Ser Ser His Pro Ile Phe His Arg Gly Glu Phe Ser Val
1               5                   10
```

<210> SEQ ID NO 3
<211> LENGTH: 178
<212> TYPE: PRT
<213> ORGANISM: Homo sapiens

<400> SEQUENCE: 3

```
Met His Ser Ser Ala Leu Leu Cys Cys Leu Val Leu Leu Thr Gly Val
```

```
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn


<210> SEQ ID NO 4
<211> LENGTH: 160
<212> TYPE: PRT
<213> ORGANISM: Artificial Sequence
<220> FEATURE:
<223> OTHER INFORMATION: Synthetic construct

<400> SEQUENCE: 4

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160


<210> SEQ ID NO 5
<211> LENGTH: 18
<212> TYPE: PRT
<213> ORGANISM: Artificial Sequence
```

<220> FEATURE:
<223> OTHER INFORMATION: Synthetic construct

<400> SEQUENCE: 5

Met His Ser Ser Ala Leu Leu Cys Cys Leu Val Leu Leu Thr Gly Val
1 5 10 15

Arg Ala

<210> SEQ ID NO 6
<211> LENGTH: 4
<212> TYPE: PRT
<213> ORGANISM: Artificial Sequence
<220> FEATURE:
<223> OTHER INFORMATION: Synthetic construct

<400> SEQUENCE: 6

Gly Gly Ser Gly
1

<210> SEQ ID NO 7
<211> LENGTH: 200
<212> TYPE: PRT
<213> ORGANISM: Artificial Sequence
<220> FEATURE:
<223> OTHER INFORMATION: Synthetic construct

<400> SEQUENCE: 7

Met His Ser Ser Ala Leu Leu Cys Cys Leu Val Leu Leu Thr Gly Val
1 5 10 15

Arg Ala Gly Gly Ser Gly Ser Ser Ser His Pro Ile Phe His Arg Gly
20 25 30

Glu Phe Ser Val Gly Gly Ser Gly Ser Pro Gly Gln Gly Thr Gln Ser
35 40 45

Glu Asn Ser Cys Thr His Phe Pro Gly Asn Leu Pro Asn Met Leu Arg
50 55 60

Asp Leu Arg Asp Ala Phe Ser Arg Val Lys Thr Phe Phe Gln Met Lys
65 70 75 80

Asp Gln Leu Asp Asn Leu Leu Leu Lys Glu Ser Leu Leu Glu Asp Phe
85 90 95

Lys Gly Tyr Leu Gly Cys Gln Ala Leu Ser Glu Met Ile Gln Phe Tyr
100 105 110

Leu Glu Glu Val Met Pro Gln Ala Glu Asn Gln Asp Pro Asp Ile Lys
115 120 125

Ala His Val Asn Ser Leu Gly Glu Asn Leu Lys Thr Leu Arg Leu Arg
130 135 140

Leu Arg Arg Cys His Arg Phe Leu Pro Cys Glu Asn Lys Ser Lys Ala
145 150 155 160

Val Glu Gln Val Lys Asn Ala Phe Asn Lys Leu Gln Glu Lys Gly Ile
165 170 175

Tyr Lys Ala Met Ser Glu Phe Asp Ile Phe Ile Asn Tyr Ile Glu Ala
180 185 190

Tyr Met Thr Met Lys Ile Arg Asn
195 200

<210> SEQ ID NO 8
<211> LENGTH: 726
<212> TYPE: DNA
<213> ORGANISM: Homo sapiens

<400> SEQUENCE: 8
atgtccatgt tgttctacac tctgatcaca gcttttctga tcggcataca ggcggaacca 60
cactcagaga gcaatgtccc tgcaggacac accatccccc aagcccactg gactaaactt 120
cagcattccc ttgacactgc ccttcgcaga gcccgcagcg ccccggcagc ggcgatagct 180
gcacgcgtgg cggggcagac ccgcaacatt actgtggacc ccaggctgtt taaaaagcgg 240
cgactccgtt caccccgtgt gctgtttagc acccagcctc cccgtgaagc tgcagacact 300
caggatctgg acttcgaggt cggtggtgct gccccettca acaggactca caggagcaag 360
cggtcatcat cccatcccat cttccacagg ggcgaattct cggtgtgtga cagtgtcagc 420
gtgtgggttg gggataagac caccgccaca gacatcaagg gcaaggaggt gatggtgttg 480
ggagaggtga acattaacaa cagtgtattc aaacagtact tttttgagac caagtgccgg 540
gacccaaatc ccgttgacag cgggtgccgg ggcattgact caaagcactg gaactcatat 600
tgtaccacga ctcacacctt tgtcaaggcg ctgaccatgg atggcaagca ggctgcctgg 660
cggtttatcc ggatagatac ggcctgtgtg tgtgtgctca gcaggaaggc tgtgagaaga 720
gcctga 726

<210> SEQ ID NO 9
<211> LENGTH: 42
<212> TYPE: DNA
<213> ORGANISM: Artificial Sequence
<220> FEATURE:
<223> OTHER INFORMATION: Synthetic construct

<400> SEQUENCE: 9
tcatcatccc atcccatctt ccacaggggc gaattctcgg tg 42

<210> SEQ ID NO 10
<211> LENGTH: 537
<212> TYPE: DNA
<213> ORGANISM: Homo sapiens

<400> SEQUENCE: 10
atgcacagct cagcactgct ctgttgcctg gtcctcctga ctggggtgag ggccagccca 60
ggccagggca cccagtctga gaacagctgc acccacttcc caggcaacct gcctaacatg 120
cttcgagatc tccgagatgc cttcagcaga gtgaagactt tctttcaaat gaaggatcag 180
ctggacaact tgttgttaaa ggagtccttg ctggaggact ttaagggtta cctgggttgc 240
caagccttgt ctgagatgat ccagttttac ctggaggagg tgatgcccca agctgagaac 300
caagacccag acatcaaggc gcatgtgaac tccctggggg agaacctgaa gaccctcagg 360
ctgaggctac ggcgctgtca tcgatttctt ccctgtgaaa acaagagcaa ggccgtggag 420
caggtgaaga atgcctttaa taagctccaa gagaaaggca tctacaaagc catgagtgag 480
tttgacatct tcatcaacta catagaagcc tacatgacaa tgaagatacg aaactga 537

<210> SEQ ID NO 11
<211> LENGTH: 483
<212> TYPE: DNA
<213> ORGANISM: Artificial Sequence
<220> FEATURE:
<223> OTHER INFORMATION: Synthetic construct

<400> SEQUENCE: 11
agcccaggcc agggcaccca gtctgagaac agctgcaccc acttcccagg caacctgcct 60
aacatgcttc gagatctccg agatgccttc agcagagtga agactttctt tcaaatgaag 120

-continued

```
gatcagctgg acaacttgtt gttaaaggag tccttgctgg aggactttaa gggttacctg    180

ggttgccaag ccttgtctga gatgatccag ttttacctgg aggaggtgat gccccaagct    240

gagaaccaag acccagacat caaggcgcat gtgaactccc tgggggagaa cctgaagacc    300

ctcaggctga ggctacggcg ctgtcatcga tttcttccct gtgaaaacaa gagcaaggcc    360

gtggagcagg tgaagaatgc ctttaataag ctccaagaga aaggcatcta caaagccatg    420

agtgagtttg acatcttcat caactacata gaagcctaca tgacaatgaa gatacgaaac    480

tga                                                                  483


<210> SEQ ID NO 12
<211> LENGTH: 54
<212> TYPE: DNA
<213> ORGANISM: Artificial Sequence
<220> FEATURE:
<223> OTHER INFORMATION: Synthetic construct

<400> SEQUENCE: 12

atgcacagct cagcactgct ctgttgcctg gtcctcctga ctggggtgag ggcc           54


<210> SEQ ID NO 13
<211> LENGTH: 12
<212> TYPE: DNA
<213> ORGANISM: Artificial Sequence
<220> FEATURE:
<223> OTHER INFORMATION: Synthetic construct

<400> SEQUENCE: 13

ggaggatcag gc                                                         12


<210> SEQ ID NO 14
<211> LENGTH: 603
<212> TYPE: DNA
<213> ORGANISM: Artificial Sequence
<220> FEATURE:
<223> OTHER INFORMATION: Synthetic construct

<400> SEQUENCE: 14

atgcacagct cagcactgct ctgttgcctg gtcctcctga ctggggtgag ggccggagga     60

tcaggctcat catcccatcc catcttccac aggggcgaat tctcggtggg aggatcaggc    120

agcccaggcc agggcaccca gtctgagaac agctgcaccc acttcccagg caacctgcct    180

aacatgcttc gagatctccg agatgccttc agcagagtga agactttctt tcaaatgaag    240

gatcagctgg acaacttgtt gttaaaggag tccttgctgg aggactttaa gggttacctg    300

ggttgccaag ccttgtctga gatgatccag ttttacctgg aggaggtgat gccccaagct    360

gagaaccaag acccagacat caaggcgcat gtgaactccc tgggggagaa cctgaagacc    420

ctcaggctga ggctacggcg ctgtcatcga tttcttccct gtgaaaacaa gagcaaggcc    480

gtggagcagg tgaagaatgc ctttaataag ctccaagaga aaggcatcta caaagccatg    540

agtgagtttg acatcttcat caactacata gaagcctaca tgacaatgaa gatacgaaac    600

tga                                                                  603
```